United States Patent [19]

Kobylecki et al.

[11] 4,241,066
[45] Dec. 23, 1980

[54] 14-AMINO DERIVATIVES OF MORPHINE, METHODS OF MAKING THEM AND ANALGESIC COMPOSITIONS CONTAINING THEM

[75] Inventors: Ryszard J. Kobylecki, Patrington; Ian G. Guest, Burstwick; John W. Lewis, North Ferriby, all of England; Gordon W. Kirby, Glasgow, Scotland

[73] Assignee: Reckitt & Colman Products Limited, London, England

[21] Appl. No.: 886,833

[22] Filed: Mar. 15, 1978

[30] Foreign Application Priority Data

Mar. 23, 1977 [GB] United Kingdom ............... 12325/77

[51] Int. Cl.² ................. A61K 31/485; C07D 489/06
[52] U.S. Cl. .................................... 424/260; 546/44; 546/45; 542/403
[58] Field of Search .................. 260/285; 424/260; 542/403; 546/44, 45

[56] References Cited

U.S. PATENT DOCUMENTS

| | | | |
|---|---|---|---|
| 3,322,771 | 5/1967 | Bartels-Keith | 260/285 |
| 3,332,950 | 7/1967 | Blumberg et al. | 260/285 |
| 3,393,197 | 7/1968 | Pachter et al. | 260/285 |
| 3,819,635 | 6/1974 | Pachter et al. | 260/285 |
| 4,017,497 | 4/1977 | Lim et al. | 260/285 |
| 4,089,855 | 5/1978 | Chatterjie et al. | 260/285 |

OTHER PUBLICATIONS

Bentley et al., Chemical Communications (1969), p. 1411.
Allen et al., Chemical Communications (1970), p. 1346.
Fieser et al., Advanced Organic Chemistry, New York, Reinhold Publishing Corp. (1961), p. 707.
Noller, Chemistry of Organic Compounds, 3rd Ed., W. B. Saunders Co., New York, (1965), p. 282.
Joshi et al., Chemical Abstracts, vol. 43, 7438c (1949).
Arnold, Chemical Abstracts, vol. 78, 98,250q (1973).
Fieser et al., "Reagents for Organic Synthesis", John Wiley & Sons, N.Y. (1967), pp. 1081-1082.
Allen, R. M., "Synthesis of New Codeinone & Indolinocodeinone Derivatives," Thesis Submitted to Loughborough University of Technology, 9/71, cited in Index to Theses, vol. XXII, 1971-1972 ed., Paterson et al., Aslib, London (1974).
Rice, Journal of Medicinal Chemistry, vol. 20, No. 1, pp. 164-165 (1/77).

*Primary Examiner*—Jose Tovar
*Assistant Examiner*—Diana G. Rivers
*Attorney, Agent, or Firm*—Bacon & Thomas

[57] ABSTRACT

Novel derivatives of morphine having the general formula:

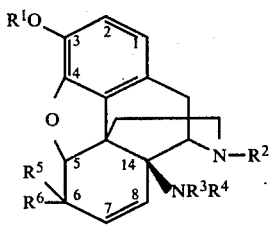

wherein $R^1$, $R^2$, $R^3$, $R^4$, $R^5$ and $R^6$ are certain specified values, and their pharmaceutically acceptable salts.

The compounds exhibit activity in the central nervous system and may be presented in the form of pharmaceutical compositions comprising a compound of formula (I), or a pharmaceutically acceptable salt thereof, in association with a pharmaceutically acceptable diluent or carrier.

17 Claims, No Drawings

14-AMINO DERIVATIVES OF MORPHINE, METHODS OF MAKING THEM AND ANALGESIC COMPOSITIONS CONTAINING THEM

This invention relates to derivatives of morphine, to processes for their preparation and to pharmaceutical compositions thereof.

According to this invention there are provided compounds of the formula:

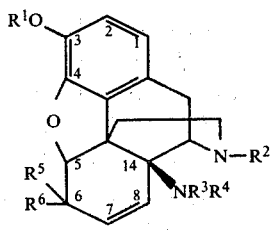

wherein
$R^1$ is hydrogen or alkyl $C_{1-3}$;
$R^2$ is hydrogen, cycloalkyl $C_{3-7}$ alkyl $C_{1-4}$, propargyl or the group

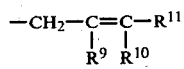

in which
$R^9$, $R^{10}$ and $R^{11}$ are hydrogen, methyl or chlorine;
$R^3$ is hydrogen, alkyl $C_{1-12}$ preferably alkyl $C_{5-8}$, alkenyl $C_{3-8}$, cycloalkyl $C_{3-7}$ alkyl $C_{1-4}$, Ar-alkyl $C_{1-5}$ or Ar-alkenyl $C_{3-5}$, provided that $R^3$ does not contain the system —CH=CH— attached to the nitrogen atom at position 14;
$R^4$ is hydrogen, alkyl $C_{1-8}$ or the group $COR^7$ in which $R^7$ is hydrogen, alkyl $C_{1-11}$, alkenyl $C_{2-7}$, Ar, Ar-alkyl $C_{1-5}$, Ar-alkenyl $C_{2-5}$, cycloalkyl $C_{3-8}$, cycloalkyl $C_{3-8}$ alkyl $C_{1-3}$, O alkyl $C_{1-4}$ or O-Ar;
Ar is phenyl or phenyl substituted by halogen, alkyl $C_{1-3}$, hydroxy or alkoxy $C_{1-3}$;
$R^5$ is hydrogen and $R^6$ is hydroxy; or $R^5$ and $R^6$ are together oxygen; or $R^5$ and $R^6$ may be methoxy when $R^1$ is methyl;
the dotted line indicates an optional bond; and their pharmaceutically acceptable salts.

In a further aspect of the invention there are provided compounds of formula I wherein
$R^1$ is methyl;
$R^2$ is —COY in which Y is hydrogen, alkyl $C_{1-6}$, cyclodkyl $C_{3-7}$, alkoxy $C_{1-6}$, phenoxy, benzyloxy or $\beta,\beta,\beta$-trichloroethoxy;
$R^3$ and $R^4$ are hydrogen;
$R^5$ and $R^6$ are both methoxy or are together oxygen; and the dotted line indicates a bond.

Suitable values of $R^1$ contemplated by the invention include hydrogen, methyl, ethyl and propyl.

Suitable values of $R^2$ include hydrogen, cyclopropylmethyl, cyclobutylmethyl, cyclopropylethyl, allyl, 3-methallyl, 3,3-dimethallyl, propargyl, t-butoxycarbonyl, formyl, ethoxycarbonyl, benzyloxycarbonyl, acetyl, trichloroethoxycarbonyl, phenoxycarbonyl and 3,3-dichloroallyl and 3-chloroallyl.

Suitable values of $R^3$ contemplated by the invention include hydrogen, methyl, ethyl, propyl, butyl, pentyl, hexyl, heptyl, octyl, nonyl, decyl, dodecyl, allyl, 3-methallyl, 3,3-dimethallyl, cyclopropylmethyl, cyclobutylmethyl, cyclopropylethyl, benzyl, α-phenethyl, β-phenethyl, 3-phenpropyl and 4-phenbutyl.

Suitable values of $R^4$ include hydrogen, methyl, ethyl, propyl, formyl, acetyl, propionyl, butyryl, pentanoyl, hexanoyl, heptanoyl, octanoyl, cinnamoyl, phenylacetyl, 3-phenpropionyl, 4-phenylbutyryl, cyclopropylcarbonyl and cyclobutylcarbonyl.

Halogen includes fluorine, chlorine, bromine and iodine.

The compounds of Formula I may be converted to a pharmaceutically acceptable non-toxic acid addition salt by treatment with an appropriate acid, for example, an inorganic acid, such as, hydrochloric, sulphuric or phosphoric acid, or an organic acid, such as, acetic, propionic, malonic, succinic, fumaric, tartaric, citric, benzoic or cinnamic acid.

The invention also provides pharmaceutical compositions comprising a compound of Formula I or a pharmaceutically acceptable salt thereof in association with a pharmaceutically acceptable diluent or carrier.

The compounds of Formula I exhibit pharmacological activity in animal test methods. In particular the compounds in which $R^2$ is cycloalkyl $C_{3-7}$ alkyl $C_{1-4}$, propargyl or

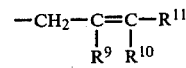

exhibit activity in the central nervous system.

The compounds of Formula I in which $R^2$ is hydrogen or —COY are mainly of use as intermediates in the preparation of other compounds of Formula I in which the substituent is replaced by another value of $R^2$ such as allyl.

The compounds of Formula I in which $R^1$ is methyl, $R^2$ is cycloalkyl $C_{3-7}$ alkyl $C_{1-4}$ or COY (where Y is as hereinbefore defined), $R^3$ and $R^4$ are hydrogen, $R^5$ and $R^6$ are both methoxy, and the optional bond is present, may be prepared by reacting an N-substituted northebaine of Formula II (where $R^x$ is cycloalkyl $C_{3-7}$ alkyl $C_{1-4}$ or —COY) with tetranitromethane in methanol followed by reduction of the resultant compound of Formula III with ammonium chloride and zinc powder in methanol:

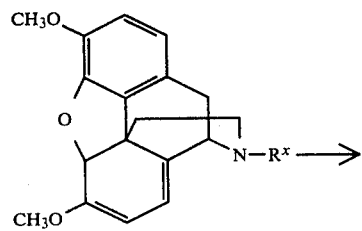

II

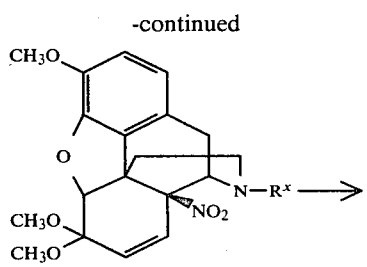

III

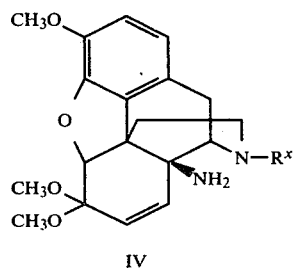

IV

The compounds of Formula III wherein $R^x$ is cycloalkyl $C_{3-7}$ alkyl $C_{1-4}$ or COY, in which Y is hydrogen, alkyl $C_{1-6}$, alkoxy $C_{1-6}$, phenoxy, benzyloxy or $\beta,\beta,\beta$-trichloroethoxy, are novel compounds and it is to be understood that the invention also includes these compounds and their methods of preparation described herein.

The compounds of Formula I in which $R^2$ is $R^x$, $R^3$ and/or $R^4$ are other than hydrogen may be prepared from the analogous compounds of Formula I in which $R^2$ is $R^x$, $R^3$ and/or $R^4$ are hydrogen by standard methods of alkylation with an organo halide $R^8X$ (where $R^8$ has the same values as $R^3$ other than hydrogen, and X is chlorine, bromine or iodine) or by acylation with for example an acyl anhydride $(R^7CO)_2O$ or chloride $R^7COCl$ (where $R^7$ is as hereinbefore defined).

The compounds of Formula I in which $R^1$ is methyl, $R^5$ and $R^6$ are both methoxy and $R^4$ is $COR^7$ and where $R^7$ is as hereinbefore defined may be reduced with for example lithium aluminium hydride to afford compounds of Formula I.

The compounds of Formula I in which $R^2$ is hydrogen may be prepared from the analogous compounds of Formula I in which $R^2$ is —COY by standard methods for the removal of N-protecting groups. Suitable methods for removing the benzyloxycarbonyl group include catalytic hydrogenolysis and the use of HBr/acetic acid, boron tribromide or trifluoracetic acid. Acyl and alkoxycarbonyl groups may be removed using aqueous hydrochloric acid or trifluoracetic acid. Phenoxycarbonyl may be removed using hydrazine hydrate. It will be appreciated that since these reagents may cause transformation in other parts of the molecule the selection of the most suitable of the reagents for deprotection will be dependent upon the final compound envisaged. In turn the selection of the protecting group will be dependent upon which deprotecting agents may be used.

The compounds of Formula I in which $R^2$ is cycloalkyl $C_{3-7}$ alkyl $C_{1-4}$, propargyl or the group $$CH_2-\underset{R^9}{C}=\underset{R^{10}}{C}-R^{11}$$

may be prepared from the analogous compounds of Formula I in which $R^2$ is hydrogen by treatment with respectively a cycloalkyl $C_{3-7}$ alkyl $C_{1-4}$ halide, propargyl halide or alkenyl halide $$X-CH_2-\underset{R^9}{C}=\underset{R^{10}}{C}-R^{11}$$

(where X is chlorine, bromine or iodine).

The compounds of Formula I in which $R^1$ is hydrogen may be prepared from the analogous compounds of Formula I in which $R^1$ is methyl by treatment with boron tribromide or boron trichloride. Conveniently the reaction is carried out in the presence of a chlorinated aliphatic hydrocarbon such as chloroform, carbon tetrachloride, tetrachloroethylene, or hexachloroethane and most conveniently in methylene chloride, at a temperature of $-50°$ to $0°$ and preferably $-30°$ to $-10°$ C.

The compounds of Formula I in which $R^1$ is hydrogen, $R^5$ and $R^6$ are together oxygen may also be prepared from the analogous compounds of Formula I in which $R^1$ is methyl and both $R^5$ and $R^6$ is methoxy by similar treatment with boron tribromide or boron trichloride.

The compounds of Formula I in which $R^1$ is hydrogen, $R^2$ is cycloalkyl $C_{3-7}$ alkyl $C_{1-4}$, $R^3$ and $R^4$ are hydrogen, $R^5$ and $R^6$ are together oxygen, and the optional bond is present (i.e. the compounds of Formula VI) may be prepared by treating compounds of Formula III with boron tribromide or boron trichloride at $-50°$ to $0°$ C., preferably $-30°$ to $-10°$ and reducing the resultant compound of Formula V with for example sodium dithionite (in Formulae III, V and VI $R^y$=cycloalkyl $C_{3-7}$alkyl $C_{1-4}$).

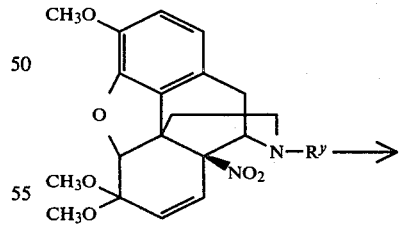

III

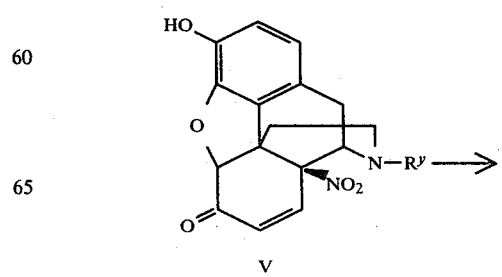

V

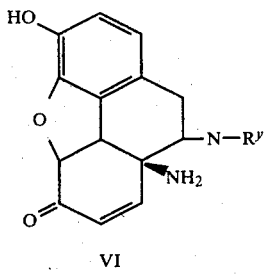

VI

The compounds of Formula I in which $R^1$ is methyl, $R^5$ and $R^6$ are together oxygen may be prepared from the analogous compounds of Formula I in which $R^1$ is methyl and both $R^5$ and $R^6$ are methoxy by treatment with an aqueous mineral acid such as hydrochloric acid.

The compounds of Formula I in which $R^5$ is hydrogen and $R^6$ is hydroxy may be prepared from the analogous compounds of Formula I in which $R^5$ and $R^6$ are together oxygen by treatment with sodium borohydride in a lower alcohol such as methanol or ethanol or by treatment with formamidine sulphinic acid.

The compounds of Formula I in which the optional bond is absent may be prepared from analogous compounds of Formula I in which the optional bond is present by hydrogenation in the presence of a catalyst such as platinium catayst or preferably a palladium catalyst such as 10% palladium on carbon, carrying out the reduction in a solvent such as ethyl acetate, methylene chloride or a lower alcohol such as methanol, ethanol or isopropanol.

The compounds of Formula I in which $R^1$ is alkyl $C_{1-3}$ may be prepared from the analogous compounds of Formula I in which $R^1$ is hydrogen by standard methods for preparing aryl ethers for example treatment of the corresponding phenoxide with an alkyl $C_{1-3}$ halide.

It is to be understood that the invention also involves the processes for the preparation of the compounds of Formula I as described herein.

The invention is illustrated by the following non-limiting Examples in which temperatures are in degrees centigrade.

EXAMPLE 1

14-β-Nitro-N-cyclopropylmethylnorcodeinone dimethyl ketal

A solution of N-cyclopropylmethylnorthebaine (1.48 g) in absolute methanol (150 ml) was purged with dry nitrogen for 15 minutes. A solution of dry ammonia in absolute methanol (3 ml) was added, followed by tetranitromethane (1.2 ml). The solution was stirred overnight (15 hours) in the dark. The methanol was removed in vacuo, and the resulting semisolid triturated with chloroform. The solid material was collected by filtration washed well with chloroform and discarded. Evaporation of the filtrate gave an orange coloured oil, which was applied to the top of a short column of grade III alumina and eluted with chloroform. The combined eluents were evaporated and gave 14-β-nitro-N-cyclopropylmethylnorcodeinone dimethyl ketal as a pale yellow solid which was recrystallised from ethanol as gleaming plates (1.21 g, 67%) m.p. 215°-6°.

EXAMPLE 2

14-β-Nitro-N-cyclobutylmethylnorcodeinone dimethyl ketal

This was prepared by the general method of Example 1, and was obtained as pale yellow gleaming plates on recrystallisation from ethanol, m.p. 213°-214°.

EXAMPLE 3

14-β-Nitro-N-phenoxycarbonylnorcodeinone dimethyl ketal

This was prepared by the general method of Example 1, and was obtained as colourless plates on recyrstallisation from a diethylether/petroleum ether (b.p. 40°-60°) mixture, m.p. 186°-187.5°.

EXAMPLE 4

14-β-Nitro-N-benzyloxycarbonylnorcodeinone dimethyl ketal

This was prepared by the general method of Example 1, and was obtained as colourless plates on recrystallisation from di-iso-propyl ether, m.p. 163°-164°.

EXAMPLE 5

14-β-Amino-N-cyclopropylmethylnorcodeinone dimethyl ketal

A hot solution of 14-β-nitro-N-cyclopropylmethylnorcodeinone dimethyl ketal (2.5 g) in absolute methanol (250 ml) was treated with zinc dust (4.0 g) and ammonium chloride (4.0 g) and heated to reflux with stirring for 1½ hours. The methanol was removed from the cooled reaction mixture in vacuo, and the residue was triturated with chloroform, the solid residues removed by filtration, and washed well with chloroform. The organic extracts were shaken with aqueous 2 N sodium hydroxide to remove zinc salts, and the chloroform layer separated, washed with water, dried and evaporated to give a colourless oil. The oil was passed down a short column of grade III alumina in chloroform to remove polar impurities and the eluents evaporated in vacuo. The oily residue crystallised on trituration with a mixture of petroleum ether/diethyl ether, the solid product was crystallised from petroleum ether (b.p. 60°-80°) to give 14-β-amino-N-cyclopropylmethylnorcodeinone dimethyl ketal as colourless chunky crystals (1.47 g, 66%) m.p. 153.5°-155°.

EXAMPLE 6

14-β-Amino-N-cyclopropylmethylnorcodeinone

A solution of 14-β-amino-N-cyclopropylmethylnorcodeinone dimethyl ketal 1.0 g) in 2 N HCl (20 ml) was allowed to stand at room temperature for 2 hours. The pH was adjusted to 7.0 with sodium bicarbonate and the resulting solution extracted with chloroform, the combined extracts were washed with water, dried and evaporated to give a colourless solid which upon recrystallisation from petroleum ether (b.p. 60°-80°) at −30° gave 14-β-amino-N-cyclopropylmethylnorcodeinone as a colourless crystalline powder (0.55 g, 70%) m.p. 122°-125°.

EXAMPLE 7

14-β-Amino-N-benzyloxycarbonylnorcodeinone dimethyl ketal

This was prepared using the general method of Example 5 and was obtained in 97% yield as a stable foam. Recrystallisation of this foam from aqueous ethanol gave 14-β-amino-N-benzyloxycarbonylnorcodeinone dimethyl ketal as a colourless microcrystalline powder, m.p. 72°–75°.

EXAMPLE 8

14-β-Methylamino-N-cyclopropylmethylnorcodeinone (a) A solution of 14-β-amino-N-cyclopropylmethylnorcodeinone dimethyl ketal (2.0 g) in 10% aqueous acetone (100 ml) was treated with sodium bicarbonate (5 g) and methyl iodide (1.07 g) and heated to reflux for 45 minutes. The solvents were removed in vacuo, the oily residue dissolved in 2 N HCl (20 ml) and kept at room temperature for 2 hours. The pH was adjusted to 7.0 with sodium bicarbonate, the solution extracted with chloroform. The combined extracts were washed, dried and evaporated in vacuo to give an oil. The desired material was separated from the mixture of products by chromatography on silica gel (chloroform/10% methanol). 14-β-Methylamino-N-cyclopropylmethylnorcodeinone (0.23 g) was obtained as yellow needles by recrystallisation from petroleum ether (60°–80°), m.p. 128°–9°.

(b) A solution of 14-β-amino-N-cyclopropylmethylnorcodeinone dimethyl ketal (4.0 g) in chloroform (60 ml) was cooled to 0°, treated with triethylamine (4 ml) and ethyl chloroformate (1.2 g) and stirred at room temperature for 1 hour. The solvents were removed in vacuo, the residue triturated with diethyl ether, the ionic salts removed by filtration, washed well with chloroform, and the filtrates evaporated. The resultant solid was added to an ice cold suspension of lithium aluminium hydride (2 g) in tetrahydrofuran (60 ml) and the resulting mixture stirred at room temperature for 24 hours. The excess lithium aluminium hydride was decomposed by addition of a saturated aqueous solution of sodium sulphate, the aluminium salts removed by filtration and washed well with chloroform. The combined extracts were evaporated, and the residue dissolved in a mixture of chloroform and 2 N HCl, and kept at room temperature for 2 hours. The pH was adjusted to 7.0 with sodium bicarbonate, the mixture extracted with chloroform, the combined extracts washed with water, dried and evaporated. The resulting oil was passed down a short column of grade III alumina to remove polar material and the eluents evaporated. The resulting oil crystallised on trituration with diethyl ether, and gave 14-β-methyl amino-N-cyclopropylmethylnorcodeinone as yellow needles from petroleum ether (b.p. 60°–80°), m.p. 128°–9°, identical to (a) above.

EXAMPLE 9

14-β-Ethylamino-N-cyclopropylmethylnorcodeinone

A solution of 14-β-amino-N-cyclopropylmethylnorcodeinone dimethyl ketal (5.0 g) in chloroform (60 ml) was cooled to 0°, treated with triethylamine (5 ml) and acetyl chloride (1.1 g) and stirred for 1 hour at room temperature. The chloroform was removed in vacuo and the resulting semi-solid triturated with diethyl ether, the ionic salts removed by filtration and washed well with diethyl ether. The filtrates were evaporated and the resulting solid reduced by portionwise addition to an ice-cold stirred suspension of lithium aluminium hydride (3 g) in tetrahydrofuran (60 ml) over 5 minutes, the resulting mixture was then stirred at room temperature for 20 hours. The excess lithium aluminium hydride was decomposed by addition of a saturated aqueous solution of sodium sulphate, the aluminium salts removed by filtration, washed well with chloroform, and the combined extracts evaporated. The residue was dissolved in a mixture of chloroform and 2 N HCl and kept at room temperature for 2 hours. The pH was adjusted to 7.0 with sodium bicarbonate, the mixture extracted with chloroform, the combined extracts washed with water, dried and evaporated to give an oil. The oil was passed down a short column of grade III alumina in chloroform to remove polar impurities, and the eluents were evaporated, to give an oil, which crystallised on trituration with diethyl ether to give 14-β-ethylamino-N-cyclopropylmethylnorcodeinone (2.18 g) as colourless rosettes from petroleum ether (b.p. 60°–80°), m.p. 166°–169.5°.

EXAMPLE 10

14-β-Cyclopropylmethylamino-N-cyclopropylmethylnorcodeinone

A solution of 14-β-amino-N-cyclopropylmethylnorcodeinone dimethyl ketal (2.5 g) in pyridine (6 ml) was cooled to 0°, treated with cyclopropylcarbonyl chloride (0.65 g) and the mixture stirred for 1 hour at room temperature. The mixture was poured into water, extracted with chloroform, the extracts washed with saturated sodium bicarbonate solution, washed well with water, dried and evaporated in vacuo to give an oil. This oil was dissolved in tetrahydrofuran (10 ml) and was reduced by dropwise addition over 5 minutes to a stirred suspension of lithium aluminium hydride (1.3 g) in tetrahydrofuran (60 ml), the suspension then being heated to reflux for 2 hours. The excess lithium aluminium hydride in the cooled reaction mixture was destroyed by the addition of a saturated aqueous solution of sodium sulphate, the aluminium salts removed by filtration and washed well with chloroform. The combined filtrates were diluted with water (100 ml), extracted with chloroform, the combined extracts washed with water, dried and evaporated in vacuo to give an oil. The oil was dissolved in a mixture of 2 N HCl and chloroform and kept for 2 hours at room temperature. The pH was adjusted to 7.0 with sodium bicarbonate, the mixture extracted with chloroform, the combined extracts washed with water, dried and evaporated. The resulting oil was passed down a short column of grade III alumina in chloroform and the eluents evaporated. The resulting oil crystallised on trituration with diethyl ether, and was recrystallised from an ether/petroleum ether (b.p. 60°–80°) mixture to give 14-β-cyclopropylmethylamino-N-cyclopropylmethylnorcodeinone (1.19 g, 47%) as colourless plates, m.p. 105°–6°.

EXAMPLE 11

14-β-Formylamino-N-cyclopropylmethylnorcodeinone

A solution of 14-β-amino-N-cyclopropylmethylnorcodeinone dimethyl ketal (2.0 g) in 90% formic acid (15 ml) was warmed to 50°–55° for 5 hours. The cooled solution was neutralised with saturated sodium bicarbonate solution, extracted into methylene chloride, the combined extracts washed with water, dried and evaporated. The solid product was recrystallised from a diethyl ether/dichloromethane/petroleum ether (b.p. 60°-80°) mixture to give 14-β-formylamino-N-cyclopropylmethylnorcodeinone (1.15 g, 60%) as long colourless needles m.p. 227°-230°.

EXAMPLE 12

14-β-Acetylamino-N-cyclopropylmethylnorcodeinone

A solution of 14-β-amino-N-cyclopropylmethylnorcodeinone dimethyl ketal (1.0 g) in pyridine (6 ml) was cooled to 0°, treated with acetic anhydride (3 ml) and stirred at room temperature for 3 hours. The pyridine was removed in vacuo, and the oily residue dissolved in 2 N HCl and stood for 2 hours at room temperature. The pH was adjusted to 7.0 with sodium bicarbonate, the mixture extracted with methylene chloride, the combined extracts washed with water, dried and evaporated in vacuo. The resulting oil was passed down a short column of grade III alumina to remove polar impurities and the eluents evaporated. Trituration with ether of the resulting oil caused crystallisation and 14-β-acetylamino-N-cyclopropylmethylnorcodeinone (0.63 g, 64%) was obtained by recrystallisation from diethyl ether/petroleum ether (b.p. 40°-60°) as long colourless needles, m.p. 189°-189.5°.

EXAMPLE 13

14-β-Propionylamino-N-cyclopropylmethylnorcodeinone

A solution of 14-β-amino-N-cyclopropylmethylnorcodeinone dimethyl ketal (2.5 g) in chloroform (60 ml) was cooled to 0° C., treated with triethylamine (2.5 ml), propionyl chloride (1.0 g) and stirred for 1 hour. The solution was treated with 2 N HCl (50 ml) and stirred for 2 hours. The mixture was neutralised with sodium bicarbonate and extracted with chloroform. The combined extracts were washed with water, dried and evaporated to give an oil which crystallised on trituration with diethyl ether. The solid product was recrystallised from an acetone/di-iso-propyl ether mixture to give 14-β-propionylamino-N-cyclopropylmethylnorcodeinone (2.48 g) as colourless gleaming plates, m.p. 221°-224°.

EXAMPLE 14

14-β-Cinnamoylamino-N-cyclopropylmethylnorcodeinone dimethyl ketal

A solution of 14-β-amino-N-cyclopropylmethylnorcodeinone dimethyl ketal (2.0 g) in pyridine (10 ml) was cooled to 0°, treated with cinnamoyl chloride (0.90 g) and stirred at room temperature overnight. The pyridine was removed in vacuo, the residue dissolved in chloroform, washed with sodium bicarbonate solution, water, dried, and evaporated in vacuo. The oily residue was passed down a short grade I alumina column in chloroform, the eluents evaporated to give an oil, which was crystallised on trituration with an ether/dioxan mixture. The solid product was collected by filtration, and was recrystallised from dioxan to give 14-β-cinnamoylamino-N-cyclopropylmethylnorcodeinone dimethyl ketal (1.32 g 55%) as colourless needles, m.p. 126°-8°.

EXAMPLE 15

14-β-Cinnamoylamino-N-cyclopropylmethylnorcodeinone (a) A solution of 14-β-amino-N-cyclopropylmethylnorcodeinone dimethyl ketal (4.0 g) in 2 N HCl (10 ml) was kept at room temperature for 2 hours. This solution was neutralised by a large excess of sodium bicarbonate, cooled to 0°, treated with water (50 ml), chloroform (100 ml) freshly prepared cinnamoyl chloride (from cinnamic acid [2.04 g]), and stirred vigorously at room temperature for 30 minutes. The chloroform layer was separated, the aqueous layer extracted with chloroform, the combined extracts washed with water, dried and evaporated. The resulting oil was passed down a short column of grade I alumina in chloroform and the eluents evaporated. The resulting oil crystallised upon trituration with diethyl ether/ethanol, the product was collected by filtration and recrystallised from diethyl ether to give 14-β-cinnamoylamino-N-cyclopropylmethylnorcodeinone (2.79 g) as colourless needle shaped crystals with m.p. 127° (A repeat preparation using identical procedures produced a product of differing crystal habit m.p. 180°-181°, identical by t.l.c., I.R., N.M.R. and elemental analysis).

(b) The compound may also be prepared by the prolonged acid hydrolysis of 14-β-cinnamoylamino-N-cyclopropylmethylnorcodeinone dimethyl ketal.

EXAMPLE 16

14-β-Dimethylamino-N-benzyloxycarbonylnorcodeinone dimethyl ketal

A solution of 14-β-amino-N-benzyloxycarbonylnorcodeinone dimethyl ketal (2.27 g) in acetone (80 ml) was treated with anhydrous potassium carbonate (5.0 g), water (10 ml), methyl iodide (50 ml) and the mixture heated to reflux for 20 hours. (After 15 minutes a colour change [from deep yellow to straw] was observed, thin layer chromatography indicating conversion to the monomethyl derivative). The acetone was removed in vacuo, the residue dissolved in water, extracted with chloroform, the combined extracts were washed with water, dried and evaporated to give the product as a crystalline solid (2.2 g).

EXAMPLE 17

14-β-Acetylamino-7,8-dihydro-N-cyclopropylmethylnormorphinone

This was prepared from 14-β-acetylamino-N-cyclopropylmethylnormorphinone by catalytic hydrogenation with Pd/C 10% in methanolic solution. The product 14-β-acetylamino-7,8-dihydro-N-cyclopropylmethylnormorphinone was obtained as long colourless needles by recrystallisation from a dichloromethane/petroleum ether (b.p. 40°-60°) mixture, m.p. 219°-220°.

EXAMPLE 18

14-β-Acetylamino-N-cyclopropylmethylnormorphine

A solution of 14-β-acetylamino-N-cyclopropylmethylnormorphinone (1.1 g) in methanol (200 ml) was treated with sodium borohydride (0.30 g) and stirred at room temperature for 1 hour. The solution was acidified with glacial acetic acid, neutralised with sodium bicarbonate, and evaporated to dryness under reduced pressure. The solid residue was triturated with dichloromethane and ionic salts removed by filtration, evaporation of the filtrate and trituration with petroleum ether gave a colourless solid. The product gave 14-β-acetylamino-N-cyclopropylmethylnormorphine (0.57 g) on recrystallisation from dichloromethane/petroleum ether (b.p. 40°-60°), melting slowly over range 193°-200°.

EXAMPLE 19

14-β-Dimethylamino-N-cyclopropylmethylnorcodeinone

A solution of 14-β-dimethylamino-N-benzyloxycarbonylnorcodeinone dimethyl ketal (2.35 g) in diethyl ether was treated at 0° with HBr/acetic acid (20 ml) and stirred at room temperature for 1½ hours. The mixture was dissolved in ice-water, extracted with petroleum ether (b.p. 40°-60°) (3x) to remove benzyl bromide, the pH adjusted to 7.0 with sodium bicarbonate, and then extracted with chloroform. The combined chloroform extracts were dried and evaporated in vacuo to give a colourless foam (1.50 g). The foam was dissolved in acetone (50 ml), treated with water (5 ml), potassium carbonate (5 g), potassium iodide (5 g), cyclopropylmethyl bromide (0.75 g) and heated under reflux for 1½ hours. The acetone was removed under reduced pressure, the residue dissolved in water, extracted with chloroform, the combined extracts washed, dried and evaporated. The resulting oil was passed down a short column of grade III alumina in ethyl acetate, and the eluents evaporated. The resulting oil crystallised on standing and was recrystallised from cyclohexane to give 14-β-dimethylamino-N-cyclopropylmethylnorcodeinone (1.01 g) as pale yellow plates, m.p. 185°-186.5°.

EXAMPLE 20

14-β-Cinnamoylaminonorcodeinone

A solution of 14-β-amino-N-benzyloxycarbonylnorcodeinone dimethyl ketal (10.0 g) in chloroform (100 ml) was cooled to 0°, treated with triethylamine (0.5 ml) and freshly prepared cinnamoyl chloride (from cinnamic acid 3.0 g) and stirred at room temperature for 1 hour. The solvents were removed in vacuo and the residue triturated with ether, the ionic salts removed by filtration and washed well with ether. The combined filtrates were evaporated in vacuo to give a colourless oil. The oil was dissolved in HBr/acetic acid (20 ml) and kept at room temperature for 2 hours. The solution was diluted with cold water, extracted with diethyl ether (3x), neutralised with sodium bicarbonate and the solution extracted with chloroform. The combined extracts were washed, dried and evaporated to give an oil which crystallised on trituration with diethyl ether. The product 14-β-cinnamoylaminonorcodeinone (6.7 g) had m.p. 175°-176°.

EXAMPLE 21

14-β-Cinnamoylamino-N-allylnorcodeinone

A solution of 14-β-cinnamoylaminonorcodeinone (2.0 g) in acetone (200 ml) was treated with water (20 ml), sodium bicarbonate (5 g), freshly distilled allyl iodide (0.86 g) and heated to reflux for 6 hours. The solvents were removed in vacuo, the residue dissolved in water (100 ml), and extracted with ethyl acetate. The combined extracts were washed with water, dried and evaporated in vacuo to give a colourless oil, which was passed down a short column of grade III alumina in ethyl acetate. The eluents were evaporated and the resulting oil crystallised on trituration with petroleum ether. The product 14-β-cinnamoylamino-N-allylnorcodeinone (0.75 g) was recrystallised from a diethyl ether/petroleum ether (b.p. 60°-80°) mixture as a colourless microcrystalline powder, m.p. 128°-131° to a clear glass.

EXAMPLE 22

14-β-Amino-N-cyclopropylmethylnormorphinone (a) A solution of 14-β-amino-N-cyclopropylmethylnorcodeinone dimethyl ketal (2.0 g) in dichloromethane (60 ml) was cooled to −60° treated with boron tribromide (3.0 ml) and the mixture stirred at −20° to −30° for 1 hour. The reaction mixture was diluted with methanol (10 ml), basified by dropwise addition of 2 N sodium hydroxide solution to pH 13, allowed to stand 5 minutes, then neutralised by passage of $CO_2$ gas. The reaction mixture was extracted with chloroform/methanol (4:1), the extracts dried and evaporated to give a brown oily solid. This was applied to a short grade III alumina column in chloroform, and eluted with chloroform/10% methanol. The pale yellow eluents were evaporated to give a yellow solid, which was recrystallised from a diethyl ether/petroleum ether (b.p. 40°-60°) mixture to give 14-β-amino-N-cyclopropylmethylnormorphinone (0.56 g, 33%) as pale yellow needles, m.p. 138°-141°.

(b) (i) A solution of 14-β-nitro-N-cyclopropylmethylnorcodeinone (or the corresponding dimethyl ketal) in methylene chloride was cooled to −60°, treated with boron tribromide and stirred at −20° to −30° for 1 hour. The reaction mixture was treated with methanol, poured into dilute sodium hydroxide solution, neutralised by passage of $CO_2$ gas, and extracted with methylene chloride. Evaporation of the extracts and recrystallisation of the resulting solid from a diethyl ether/petroleum ether (b.p. 40°-60°) mixture gave 14-β-nitro-N-cyclopropylmethylnormorphinone as pale yellow needle shaped crystals.

(ii) A solution of 14-β-nitro-N-cyclopropylmethylnormorphinone in methanol was treated with an aqueous suspension of sodium dithionite (excess) and the resulting mixture was heated to gentle reflux overnight. Removal of the solvent, extraction of the reaction residue and evaporation of the extracts gave 14-β-amino-N-cyclopropylmethylnormorphinone identical to that described in (a) above.

EXAMPLE 23

14-β-Methylamino-N-cyclopropylmethylnormorphinone

A solution of 14-β-methylamino-N-cyclopropylmethylnorcodeinone (1.0 g) in dichloromethane (60 ml) was cooled to −60°, treated with boron tribromide (1.5 ml) and stirred at −20° to −30° for 1 hour. The mixture was diluted with methanol (5 ml) poured into dilute sodium hydroxide solution, stood for 5 minutes, neutralised by passage of $CO_2$ gas, and the resulting mixture extracted with chloroform/methanol (4:1). The combined extracts were dried, evaporated in vacuo, and the resulting oil applied to a short column of grade III alumina, eluted with chloroform to remove non polar impurities, then with chloroform/10% methanol and the eluents evaporated to give a solid which was recrystallised from a diethyl ether/petroleum ether (b.p.

40°–60°) mixture to give 14-β-methylamino-N-cyclopropylmethylnormorphinone (0.44 g, 46%) as a pale yellow crystalline solid, melting above 155° with decomposition.

EXAMPLE 24

14-β-Amino-7,8-dihydro-N-cyclopropylmethylnorcodeinone dimethyl ketal

A solution of 14-β-amino-N-cyclopropylmethylnorcodeinone dimethyl ketal (2.0 g) in methanol (100 ml) was hydrogenated at atmospheric pressure over Pd/C 10% (400 mg) until hydrogen uptake ceased. The catalyst was removed by filtration, the filtrate evaporated to dryness, the resulting oil crystallised from petroleum ether (b.p. 40°–60°) at −60°. The solid was recrystallised from petroleum ether (b.p. 40°–60°) at −60° to give 14-β-amino-7,8-dihydro-N-cyclopropylmethylnorcodeinone dimethyl ketal (1.59 g, 76%) as a colourless microcrystalline solid, m.p. 108°–112°.

EXAMPLE 25

14-β-Formylamino-7,8-dihydro-N-cyclopropylmethylnorcodeinone (a) A solution of 14-β-amino-7,8-dihydro-N-cyclopropylmethylnorcodeinone dimethyl ketal (1.50 g) in 90% formic acid (15 ml) was heated to 80° for 15 hours. The cooled reaction mixture was neutralised with saturated sodium bicarbonate solution, extracted with chloroform, the combined extracts were washed with water, dried and evaporated. The resulting oil crystallised upon trituration with diethyl ether and was recrystallised from an acetone/di-iso-propyl ether mixture to give 14-β-formylamino-7,8-dihydro-N-cyclopropylmethylnorcodeinone (1.10 g, 79%) as colourless needles, m.p. 210°–213°.

(b) Catalytic reduction of an ethyl acetate solution of 14-β-formylamino-N-cyclopropylmethylnorcodeinone using Pd/C 10% at atmospheric pressure also gave 14-β-formylamino-7,8-dihydro-N-cyclopropylmethylnorcodeinone identical to (a) above.

EXAMPLE 26

14-β-Amino-N-cyclobutylmethylnorcodeinone dimethyl ketal

This was prepared by the general method of Example 5, and was obtained as colourless chunky crystals on recrystallisation from petroleum ether (b.p. 60°–80°), m.p. 133.5°–135°.

EXAMPLE 27

14-β-Amino-N-cyclobutylmethylnorcodeinone

This was prepared by the general method of Example 6, and was obtained as colourless needles on recrystallisation from petroleum ether (b.p. 60°–80°), m.p. 173°–176°.

EXAMPLE 28

14-β-Formylamino-N-cyclobutylmethylnorcodeinone

This was prepared by the general method of Example 11, and was obtained as colourless needles on recrystallisation from diethyl ether/petroleum ether (b.p. 40°–60°) mixture, m.p. 203.5°.

EXAMPLE 29

14-β-Amino-N-cyclobutylmethylnormorphinone

This was prepared by the general method of Example 23, and was obtained as fine colourless needles on recrystallisation from diethyl ether/petroleum ether (b.p. 40°–60°) mixture, m.p. 135°–138° (to glassy melt).

EXAMPLE 30

14-β-Hexanoylaminonorcodeinone (i) A solution of 14-β-amino(N-benzyloxycarbonyl)norcodeinone dimethyl ketal in dichloromethane was acylated with hexanoyl chloride using the general procedure of example 13, and the resulting dimethyl ketal was hydrolysed in a THF solution using the procedure of Example 13. The resultant 14-β-hexanoylamino-(N-benzyloxycarbonyl)norcodeinone was obtained as colourless crystals from diethyl ether, m.p. 84°–85°.

(ii) A solution of 14-β-hexanoylamino(N-benzyloxycarbonyl)norcodeinone in anisole was treated with a fresh solution of HBr/acetic acid, and stirred at room temperature for 2 hr. The mixture was poured into ice/water, extracted with ether (3x), and the extracts discarded. The aqueous layer was neutralised with conc. sodium hydroxide solution, extracted with dichloromethane, the extracts washed, dried and evaporated, to give a pale yellow oil which crystallised upon trituration with a diethyl ether/methanol mixture to give a colourless solid, which was collected by filtration, washed well with diethyl ether, and dried in vacuo, m.p. 168.5°–170°.

EXAMPLE 31

14-β-Hexanoylaminonormorphinone

A solution of 14-β-hexanoylaminonorcodeinone was dealkylated using the general procedure of Example 23, and the product was obtained as colourless chunky crystals upon recrystallisation from ethanol, m.p. 267.5°–269°.

EXAMPLE 32

14-β-Hexanoylamino(N-propargyl)norcodeinone

A solution of 14-β-hexanoylaminonorcodeinone in acetone was alkylated using the general procedure of Example 8a, and the product was obtained as colourless crystals upon crystallisation from aqueous ethanol, m.p. 162.5°–164.5°.

EXAMPLE 33

14-β-Hexanoylamino(N-dimethylallyl)norcodeinone

A solution of 14-β-hexanoylaminonorcodeinone in acetone was alkylated using the general procedure of Example 8a, and the product was obtained as colourless crystals upon crystallisation from aqueous ethanol, m.p. 252°–253°.

EXAMPLE 34

14-β-Hexanoylamino(N-3-chloroallyl)norcodeinone

A solution of 14-β-hexanoylaminonorcodeinone in acetone was alkylated using the general procedure of Example 8a, using a cis:trans mixture of isomers (20% cis:80% trans) of 1,3-dichloroprop-1-ene. Two closely similar products were isolated by partial fractional crystallisation from diethyl ether/petroleum ether (bp 40°–60°) having m.p. 81°–83° and m.p. 130°–140° respectively.

The Table describes the preparation of compounds of the formula:

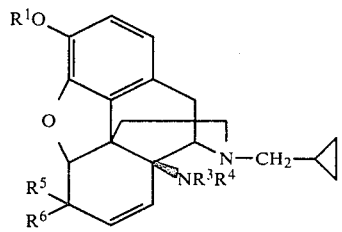

prepared as indicated by the method of the above examples, the final column of the Table giving the solvent of recrystallisation.

| Ex. | $R^1$ | $R^3$ | $R^4$ | $R^5$ | $R^6$ | Method | m.p.°C. | Solvent |
|---|---|---|---|---|---|---|---|---|
| 35 | Me | n-$C_3H_7$ | H | | =O | 9 | 115–118.5 | P |
| 36 | Me | n-$C_4H_9$ | H | | =O | 9 | 110–113.5 | P |
| 37 | Me | n-$C_5H_{11}$ | H | | =O | 9 | 89.5–90 | P |
| 38 | Me | n-$C_6H_{13}$ | H | | =O | 9 | 43–45 | P≠ |
| 39 | Me | n-$C_7H_{15}$ | H | | =O | 9 | 195–196* | A/M/E |
| 40 | Me | H | $COC_3H_7$ | | =O | 13 | 203–205.5 | DIPE/A/H |
| 41 | Me | H | $COC_4H_9$ | | =O | 13 | 176.5–178.5 | DIPE/A |
| 42 | Me | H | $COC_5H_{11}$ | | =O | 13 | 119.5–120 | E/P |
| 43 | Me | H | $COC_6H_{13}$ | | =O | 13 | 63–66 | E/P |
| 44 | H | n-$C_4H_9$ | H | | =O | 23 | 110–113.5 | E/P |
| 45 | H | n-$C_5H_{11}$ | H | | =O | 23 | 216–218 | CH |
| 46 | H | n-$C_6H_{13}$ | H | | =O | 23 | 219–224 | E/P |
| 47 | H | n-$C_7H_{15}$ | H | | =O | 23 | 168–170 | C/P |
| 48 | H | $CH_2$-c-$C_3H_5$ | H | | =O | 23 | 174–176 | CH |
| 49 | H | H | CHO | | =O | 23 | 219–221 | A/P |
| 50 | H | H | $COCH_3$ | | =O | 23 | 156–157 | E/P |
| 51 | H | H | $COC_2H_5$ | | =O | 23 | 208–213 | E/P |
| 52 | H | H | $COC_3H_7$ | | =O | 23 | 116–118 | E/P |
| 53 | H | H | $COC_4H_9$ | | =O | 23 | 114–115 | E/P |
| 54 | H | H | $COC_5H_{11}$ | | =O | 23 | 94–96 | E/P |
| 55 | H | H | $COC_6H_{13}$ | | =O | 23 | 126–128 | E/P |
| 56 | H | H | COCH=CHPh | | =O | 23 | 223–224 | E/A/P |
| 57 | H | H | $COCH_3$ | H | $OH^\Delta$ | 18 | 212–214 | DCM/P |
| 58 | Me | n-$C_8H_{17}$ | H | | =O | 9 | 166–169* | M/E |
| 59 | Me | $CH_2CH_2$-c-$C_3H_5$ | H | | =O | 9 | 124–127 | P |
| 60 | Me | $CH_2$-c-$C_8H_{15}$ | H | | =O | 9 | 126–128.5 | P |
| 61 | Me | $CH_2$-c-$C_7H_{13}$ | H | | =O | 9 | 106–109 | E/P |
| 62 | Me | $CH_2CH=CH_2$ | H | | =O | 8a | 130–132 | CH |
| 63 | Me | $(CH_2)_3CH=CH_2$ | H | | =O | 9 | 247–249 | P |
| 64 | Me | $(CH_2)_3CH=CHCH_3$ | H | | =O | 9 | 143–145* | M/E |
| 65 | Me | $CH_2Ph$ | H | | =O | 8a | 123–125 | P |
| 66 | Me | $(CH_2)_2Ph$ | H | | =O | 8a | 115–120 | E/P |
| 67 | Me | $(CH_2)_4Ph$ | H | | =O | 9 | 91–93 | P |
| 68 | Me | $(CH_2)_3$—$C_6H_4$(4-OMe) | H | | =O | 9 | 84.5–86 | P |
| 69 | Me | $(CH_2)_3$—$C_6H_4$(4-Cl) | H | | =O | 9 | 96–97.5 | P |
| 70 | Me | $(CH_2)_3$—$C_6H_4$(4-Me) | H | | =O | 9 | 120–121 | P |
| 71 | Me | $CH_2CH=CH$ Ph | H | | =O | 8a | 114–116.5 | E/P |
| 72 | Me | $(CH_2)_3CH=CH$ Ph | H | | =O | 9 | 135–136* | M/E |
| 73 | Me | H | CO—$C_7H_{15}$ | | =O | 13 | 56–59 | E/P |
| 74 | Me | H | CO-c-$C_3H_5$ | | =O | 13 | 232–235 | Et |
| 75 | Me | H | $COCH_2$-c-$C_2H_5$ | | =O | 13 | 198.5–200.5 | Et |
| 76 | Me | H | CO-c-$C_7H_{13}$ | | =O | 13 | 106–109 | E/P |
| 77 | Me | H | CO-c-$C_8H_{15}$ | | =O | 13 | 81–85 | E/P |
| 78 | Me | H | $COCH=CH_2$ | | =O | 13 | 196–198 | E/P |
| 79 | Me | H | $COCH=CHCH_3$ | | =O | 13 | 180–183 | E/P |
| 80 | Me | H | $COCH=C(CH_3)_2$ | | =O | 13 | 148–150 | E/P |
| 81 | Me | H | $CO(CH_2)_2CH=CH_2$ | | =O | 13 | 157–158 | E/P |
| 82 | Me | H | $CO(CH_2)_2CH=CHCH_3$ | | =O | 13 | 93–95 | Et/W |
| 83 | Me | H | $COCH=CHCH_2CH_3$ | | =O | 13 | 124–128 | E/P |
| 84 | Me | H | CO Ph | | =O | 13 | 265–267 | Et |
| 85 | Me | H | $COCH_2Ph$ | | =O | 13 | 186–187 | E/P |
| 86 | Me | H | $CO(CH_2)_3Ph$ | | =O | 13 | 110.5–115 | Et/W |
| 87 | Me | H | $CO(CH_2)_2$—$C_6H_4$(4-OMe) | | =O | 13 | 180.5–182.5 | Et/W |
| 88 | Me | H | $CO(CH_2)_2$—$C_6H_4$(4-Cl) | | =O | 13 | 92–94.5 | DIPE |
| 89 | Me | H | $CO(CH_2)_2$—$C_6H_4$(4-Me) | | =O | 13 | 87–88.5 | DIPE/P |
| 90 | Me | H | COCH=CH—$C_6H_4$(4-OMe) | | =O | 13 | 235–242 | DIPE |
| 91 | Me | H | COCH=CH—$C_6H_4$(4-Cl) | | =O | 13 | 201–206 | DIPE |
| 92 | Me | H | COCH=CH$C_6H_4$(4-Me) | | =O | 13 | 175.5–177 | DIPE |
| 93 | Me | H | COCH=CH—$C_6H_3$(3,4-Cl) | | =O | 13 | 221–223.5 | E/P |
| 94 | Me | H | $CO(CH_2)_2CH=CH$ Ph | | =O | 13 | 92–94 | E/P |
| 95 | H | n-$C_8H_{17}$ | H | | =O | 23 | 147–148 | CH |
| 96 | H | $CH_2CH_2$-c-$C_3H_5$ | H | | =O | 23 | 107.5–109 | CH |
| 97 | H | $CH_2$-c-$C_7H_{13}$ | H | | =O | 23 | 169–173 | E/P |

-continued

| Ex. | R¹ | R³ | R⁴ | R⁵ | R⁶ | Method | m.p.°C. | Solvent |
|---|---|---|---|---|---|---|---|---|
| 98 | H | $CH_2$-c-$C_8H_{15}$ | H | = | O | 23 | 122–125 | CH |
| 99 | H | $CH_2CH=CH_2$ | H | = | O | 23 | 185–186 | CH |
| 100 | H | $(CH_2)_3CH=CHCH_3$ | H | = | O | 23 | 174–177* | M/E |
| 101 | H | $CH_2Ph$ | H | = | O | 23 | 196–197 | CH |
| 102 | H | $(CH_2)_2Ph$ | H | = | O | 23 | 212–214 | E/P |
| 103 | H | $(CH_2)_4Ph$ | H | = | O | 23 | 154–156 | CH |
| 104 | H | $(CH_2)_3$—$C_6H_4$(4-OH) | H | = | O | 23 | 83–85 | E/P |
| 105 | H | $(CH_2)_3$—$C_6H_4$(4-Cl) | H | = | O | 23 | 190–194 | CH |
| 106 | H | $(CH_2)_3$—$C_6H_4$(4-Me) | H | = | O | 23 | 97–101 | CH |
| 107 | H | $CH_2CH=CH\,Ph$ | H | = | O | 23 | 120–122 | E/P |
| 108 | H | H | CHO | = | O▲ | 23 | 244–245 | E/P |
| 109 | H | H | CO—$C_7H_{15}$ | = | O | 23 | 136–138 | E/P |
| 110 | H | H | CO-c-$C_3H_5$ | = | O | 23 | 245–246 | Et/W |
| 111 | H | H | $COCH_2$-c-$C_3H_5$ | = | O | 23 | 215–217 | E/P |
| 112 | H | H | CO-c-$C_7H_{13}$ | = | O | 23 | 122–124 | E/P |
| 113 | H | H | $COCH=CH_2$ | = | O | 23 | 122–126 | E/P |
| 114 | H | H | $COCH=CHCH_3$ | = | O | 23 | 115–120 | E/P |
| 115 | H | H | $COCH=C(CH_3)_2$ | = | O | 23 | 152–155.5 | E/P |
| 116 | H | H | $CO(CH_2)_2CH=CH_2$ | = | O | 23 | 131–133 | E/P |
| 117 | H | H | $CO(CH_2)_2CH=CHCH_3$ | = | O | 23 | 170–174 | E/P |
| 118 | H | H | $COCH=CHCH_2CH_3$ | = | O | 23 | 122–124 | E/P |
| 119 | H | H | COPh | = | O | 23 | 180–183 | E/P |
| 120 | H | H | $COCH_2Ph$ | = | O | 23 | 220–222.5 | E/P |
| 121 | H | H | $CO(CH_2)_3Ph$ | = | O | 23 | 163–167 | CH |
| 122 | H | H | $CO(CH_2)_2$—$C_6H_4$(4-Me) | = | O | 23 | 208–209 | Et/W |
| 123 | H | H | $COCH=CH$—$C_6H_4$(4-OH) | = | O | 23 | 163–165 | E/P |
| 124 | H | H | $COCH=CH$—$C_6H_4$(4-Cl) | = | O | 23 | 279–281.5 | Et |
| 125 | H | H | $COCH=CHC_6H_4$(4-Me) | = | O | 23 | 263.5–266 | Et |
| 126 | H | H | $COCH=CH$—$C_6H_3$(3,4-Cl) | = | O | 23 | 198–201* | M/E |
| 127 | H | $CH_3$ | $CH_3$ | = | O | 23 | 116–117d | CH |

Footnotes to Table
▲ 7,8 dihydro
*hydrochloride
≠ low temperature crystallisation
(d) decomposition
Solvents of crystallisation
A = acetone
C = chloroform
D = dioxan
E = diethyl ether
H = hexane
M = methanol
P = petroleum ether (60–80°)
DCM = dichloromethane
DIPE = di-iso-propyl ether
CH = cyclohexane
Et = ethanol
W = water The compounds of the invention exhibit pharmacological actions mediated by opiate receptors. They have activity when tested in the presence and/or absence of a standard agonist (etorphine) in the transmurally stimulated mouse vas deferens preparation described by Henderson G., Hughes J., Kosterlitz, H., (Brit. J. Pharmacol. 46, 764. [1972])

In the above mentioned test method of Henderson et al male albino mice (OLA MFI strain) are killed by a blow on the head and the vasa deferentia removed and set up in an isolated organ bath of 2½ ml volume. A 'twitch' response is produced by low frequency (0.1 Hz) stimulation with 0.1 msec rectilinear pulses. The response is depressed by a large number of different pharmacologically active agents (local anaesthetics, smooth muscle depressants, adrenergic neuron blocking agents, presynaptic α-receptor stimulants, β-stimulants and narcotic agonists) but it is possible to differentiate between depression of twitch produced by narcotic agonists and depression produced by other mechanisms, by repeating the test in the presence of the narcotic antagonist naloxone (The test has been shown to be an extremely specific method of detecting narcotic agonist and antagonist activity [Hughes J., Kosterlitz H., Leslie F. M., Brit. J. Pharmacol 51, 139–140])

Narcotic antagonist action of the compounds of the invention was determined by the ability of the compounds to antagonise the opiate receptor—mediated effect elicted by etorphine in this tissue.

The compounds have been screened for agonist activity in the rat using tail pressure as the nociceptive stimulus as described by Green, H. F., and Young, P. A., Br. J. Pharmac. Chemother., 6, 572 (1951) and for morphine antagonist activity in rat using a tail flick test modified from the method described for mice by Ben Bassat et al (Arch Int. Pharmacoldyn. 122, 434 [1959]). The nociceptive stimulus in this test is a hot water bath (55° C.).

Compounds exhibiting activity in the above antinociceptive screen are agonists or partial agonists at the opiate receptor population and may have clinical utility, inter alia, as analgesics or antidiarrhoeals. In the above in vivo agonist test, the compound of Example 54 when administered subcutaneously had an $ED_{50}$ of 0.0036 mg/Kg and that of compound of Example 38 when administered subcutaneously had an $ED_{50}$ of 1.92 mg/Kg. (In this test, morphine [S.C.] had an $ED_{50}$ of 0.66 mg/Kg).

Compounds exhibiting activity in the above morphine antagonist screen are antagonists or partial agonists at the opiate receptor population and may find clinical utility, inter alia, as analgesics, as antagonists for use in cases of opiate intoxication, as antagonists for the reversal of opiate effects and as maintenance agents for use in the treatment of opiate addiction. In the above in vivo antagonist test the compound of Example 49 when administered subcutaneously had an $AD_{50}$ of 0.132 mg/Kg and the compound of Example 48 when administered subcutaneously had an $AD_{50}$ of 0.0027 mg/Kg (In this test, naloxone (S.C.) had an $AD_{50}$ of 0.0056 mg/Kg).

The therapeutic compositions may be in a form suitable for oral, rectal or parenteral aministration. Such oral compositions may be in the form of capsules, tablets, granules or liquid preparations such as elixirs, syrups or suspensions.

Tablets contain as active ingredient a compound of Formula I (or a pharmaceutically acceptable salt thereof) in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the active ingredient mixed with an inert solid diluent such as calcium phosphate, lactose or kaolin in a hard gelatine capsule.

Compositions for rectal administration in the form of suppositories may contain in addition to the active ingredient excipients such as cocoa butter or a suppository wax.

Compositions intended for parenteral administration may be in the form of a sterile preparation such as solutions in for example water, saline, buffered saline or polyhydroxy alcohols such as propylene glycol or polyethylene glycols.

For the purposes of convenience and accuracy of dosing the compositions are advantageously employed in unit dosage form. For oral administration the unit dosage form may contain 0.1 to 10 mg of the compound of Formula I or an equivalent amount of a pharmaceutically acceptable salt thereof. Parenteral unit dosage forms may contain from 0.01 mg to 10 mg of the said compound (or salt thereof) per 1 ml of the preparation.

We claim:

1. A compound of the formula:

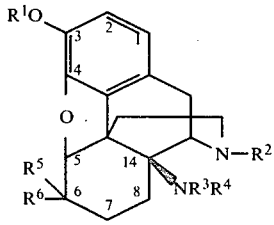

(1)

wherein $R^1$ is hydrogen $R^3$ is hydrogen, alkyl $C_{1-12}$, alkenyl $C_{3-8}$, cycloalkyl $C_{3-7}$ alkyl $C_{1-4}$, Ar-alkyl $C_{1-5}$ or Ar-alkenyl $C_{3-5}$, provided that $R^3$ does not contain the system —CH=CH— attached to the nitrogen atom at position 14;

$R^4$ is hydrogen, alkyl $C_{1-8}$ or the group $COR^7$ in which $R^7$ is hydrogen, alkyl $C_{1-11}$, alkenyl $C_{2-7}$, Ar, Ar-alkyl $C_{1-5}$, Ar-alkenyl $C_{2-5}$, cycloalkyl $C_{3-8}$, cycloalkyl $C_{3-8}$ alkyl $C_{1-3}$, O-alkyl $C_{1-4}$ or O-Ar;

Ar is phenyl or phenyl substituted by halogen, alkyl $C_{1-3}$, hydroxy or alkoxy $C_{1-3}$;

$R^5$ is hydrogen and $R^6$ is hydroxy; or $R^5$ and $R^6$ are together oxygen;

the dotted line indicates an optional bond;

$R^2$ is hydrogen, cycloalkyl $C_{3-7}$ alkyl $C_{1-4}$, propargyl or the group

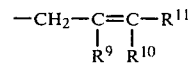

in which $R^9$, $R^{10}$ and $R^{11}$ are hydrogen, methyl or chlorine; and its pharmaceutically acceptable salts.

2. The compound of claim 1 which is 14-β-hexanoylaminonormorphinone

3. The compound of claim 1 which is 14-β-hexylamino-N-cyclopropylmethylnormorphinone.

4. The compound of claim 1 which is 14-β-cinnamoylaminonormorphinone.

5. The compound of claim 1 which is 14-β-cinnamoylamino-N-cyclopropylmethylnormorphinone.

6. The compound of claim 1 which is 14-β-heptanoylamino-N-cyclopropylmethylnormorphinone.

7. The compound of claim 1 which is 14-β-hexanoylamino-N-cyclopropylmethylnormorphinone.

8. The compound of claim 1 which is 14-β-amino-N-cyclopropylmethylnormorphinone.

9. The compound of claim 1 which is 14-β-formylamino-N-cyclopropylmethylnormorphinone.

10. The compound of claim 1 which is 14-β-methylamino-N-cyclopropylmethylnormorphinone.

11. The compound of claim 1 which is 14-β-cyclopropylmethylamino-N-cyclopropylmethyl-normorphinone.

12. A process for the preparation of a compound of Formula I as claimed in claim 1 wherein $R^1$ is hydrogen which process comprises treating a compound of Formula I in which $R^1$ is methyl with boron tribromide at a temperature in the range of from −30° to −10° C.

13. A process for the preparation of a compound of Formula I as claimed in claim 1 wherein $R^1$ is hydrogen and $R^5$ and $R^6$ are together oxygen which process comprises treating a compound of Formula I in which $R^1$ is methyl and both $R^5$ and $R^6$ are methoxy with boron tribromide at a temperature in the range of from −30° to −10° C.

14. A process for the preparation of a compound of Formula I as claimed in claim 1 wherein $R^1$ is hydrogen, $R^2$ is cycloalkyl $C_{3-7}$ alkyl $C_{1-4}$, $R^3$ and $R^4$ are hydrogen, $R^5$ and $R^6$ are together oxygen and the optional bond is present which process comprises treating a compound of Formula III in which $R^x$ is cycloalkyl $C_{3-7}$ alkyl $C_{1-4}$ with boron tribromide at a temperature in the range of from −30° to −10° C., and reducing the resultant product with sodium dithionite.

15. A pharmaceutical composition for the relief of pain which comprises at least one compound as claimed in claim 1 or a pharmaceutically acceptable salt thereof together with a pharmaceutically acceptable diluent or carrier.

16. A pharmaceutical composition for the relief of pain according to claim 15 in unit dosage form for oral administration which contains from 0.1 to 10 mg of the said compound or salt thereof per unit dosage.

17. A pharmaceutical composition for the relief of pain according to claim 15 in unit dosage form for parenteral administration which contains from 0.01 to 10 mg of the said compound or salt thereof per 1 ml of the composition

* * * * *

UNITED STATES PATENT AND TRADEMARK OFFICE
CERTIFICATE OF CORRECTION

PATENT NO. : 4,241,066   Page 1 of 3

DATED : December 23, 1980

INVENTOR(S) : Ryszard J. Kobylecki et al

It is certified that error appears in the above—identified patent and that said Letters Patent is hereby corrected as shown below:

IN THE ABSTRACT:

Please correct the structural formula to read:

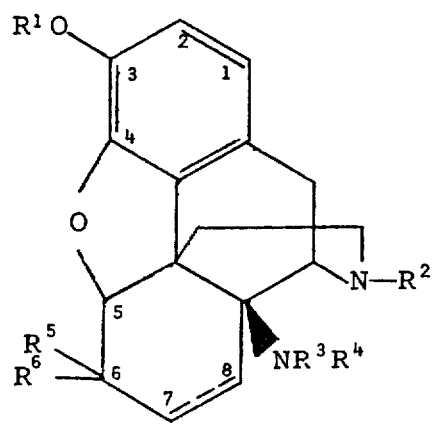

UNITED STATES PATENT AND TRADEMARK OFFICE
CERTIFICATE OF CORRECTION

PATENT NO. : 4,241,066
DATED : December 23, 1980
INVENTOR(S) : Ryszard J. Kobylecki et al It is certified that error appears in the above—identified patent and that said Letters Patent is hereby corrected as shown below:

IN THE SPECIFICATION:

Column 1, please correct the structural formula to read:

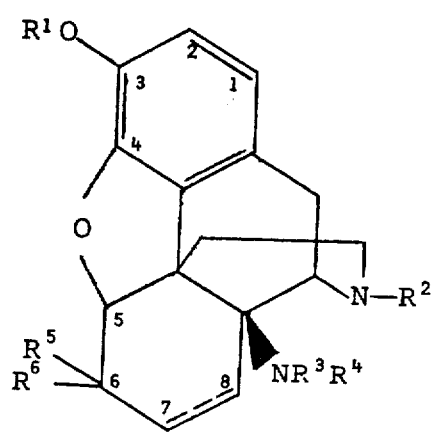

UNITED STATES PATENT AND TRADEMARK OFFICE
CERTIFICATE OF CORRECTION

PATENT NO. : 4,241,066                          Page 3 of 3

DATED        : December 23, 1980

INVENTOR(S) : Ryszard J. Kobylecki et al

It is certified that error appears in the above—identified patent and that said Letters Patent is hereby corrected as shown below:

IN THE CLAIMS:

Claim 1, line 2, please correct the structural formula to read:

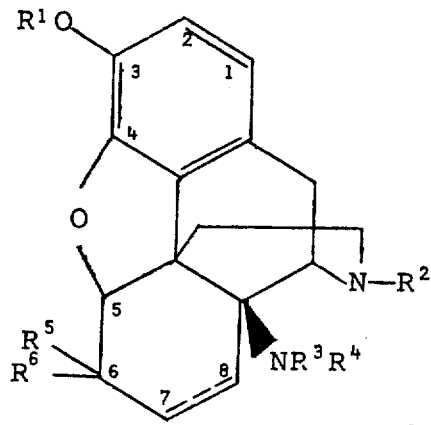

Signed and Sealed this

Second Day of June 1981

[SEAL]

Attest:

RENE D. TEGTMEYER

*Attesting Officer*         *Acting Commissioner of Patents and Trademarks*